United States Patent [19]

Li

[11] 3,942,527

[45] Mar. 9, 1976

[54] BLOOD OXYGENATION PROCESS

[75] Inventor: Norman N. Li, Edison, N.J.

[73] Assignee: Exxon Research & Engineering Co., Linden, N.J.

[22] Filed: Jan. 15, 1974

[21] Appl. No.: 433,573

Related U.S. Application Data

[63] Continuation of Ser. No. 234,644, March 14, 1972, abandoned.

[52] U.S. Cl.............................. 128/214 R; 195/1.8
[51] Int. Cl.².... A61M 1/03; C12B 3/00; C12B 9/00
[58] Field of Search..................... 195/1.8; 23/258.5; 128/214 R

[56] References Cited
UNITED STATES PATENTS

| 3,389,078 | 6/1968 | Elzinga et al. | 210/21 |
| 3,396,510 | 8/1968 | Ward et al. | 55/16 |

OTHER PUBLICATIONS deFilippi et al., *Artificial Heart Program Conference, Proceedings*, June 9–13, 1969, pp. 381–391.

*Primary Examiner*—Richard L. Huff
*Attorney, Agent, or Firm*—Robert J. Baran

[57] ABSTRACT

A process for oxygenating blood which comprises, contacting an emulsion, the exterior phase of which comprises an oxygen saturated fluorinated organic compound surrounding aqueous droplets containing a carbon dioxide absorbent or reactant, with mammalian blood. The oxygen permeates rapidly from the fluorocarbon into the blood, while the $CO_2$ within the blood permeates through the fluorocarbon into the aqueous interior phase wherein it is absorbed or converted by a reactant to a nonpermeable form. In this manner the blood is oxygenated and $CO_2$ is simultaneously removed.

8 Claims, No Drawings

BLOOD OXYGENATION PROCESS

This is a continuation, division, of application Ser. No. 234,644 filed Mar. 14, 1972.

BACKGROUND OF THE INVENTION

Field of the Invention

A process for oxygenating blood which comprises, contacting an emulsion, the exterior phase of which comprises an oxygen saturated fluorinated organic compound surrounding aqueous droplets containing a carbon dioxide absorbent or reactant, with mammalian blood. The oxygen permeates rapidly from the fluorocarbon into the blood, while the $CO_2$ within the blood permeates through the fluorocarbon into the aqueous interior phase wherein it is absorbed or converted by a reactant to a nonpermeable form. In this manner the blood is oxygenated and $CO_2$ is simultaneously removed.

2. Cross-Reference to Related Applications

This application is a Continuation-in-part of application Ser. No. 72,830, filed Sept. 16, 1970, in the name of Norman N. Li.

SUMMARY OF THE PRIOR ART

Lung disease is increasing at a very rapid rate. Emphysema and similar diseases in which the body fails to properly oxygenate the blood cause a tremendous strain on the heart and eventually lead to premature death. To increase the oxygen pressure in the bloodstream, several artificial lungs have been developed. Most commercial artificial lung devices operate by contacting the blood directly with oxygen.

Unfortunately, these devices are expensive and have met with limited success. More significantly, they have had the problem of blood coagulation or clotting because of the denaturation of proteins in the blood.

At a recent Artifical Heart Program conference held under the auspices of the U.S. Department of Health, Education, and Welfare, a liquid-liquid blood oxygenator was described whereby oxygen-saturated perfluorotributylamine was used to overcome the problems of direct contact of oxygen with blood. The developers of this system, R. P. De Filippi, R. M. Anderson, K. H. Porter, D. W. Harris of Cambridge, Massachusetts and Yukihiko Nosë of the Cleveland Clinic, Cleveland, Ohio utilized a falling film technique wherein a falling film of oxygen saturated fluorocarbon contacts a rising column of blood. Oxygen and carbon dioxide transfer occurs across the moving interface between the two immiscible liquids and thus the need for solid membranes or direct oxygen-blood contact is removed. The developers of this system depend on high interfacial velocities in the countercurrent liquid-liquid contacting to obtain high mass transfer rates. Further, while not specifically stated by the developers, carbon dioxide removal will be directly proportional to the amount of fluorocarbon present since the transfer of carbon dioxide is dependent only on its solubility in fluorocarbon.

Thus a method is needed by means of which blood can be efficiently oxygenated, while not having to rely on utilization of large amounts of the rather expensive fluorocarbons needed in the prior art processes.

Separation by means of emulsions are known in the prior art. See for example U.S. Pat. Ser. Nos. 3,389,078, 3,410,794, 3,454,489 and 3,617,546. None of these references, individually or in combination, teach, show or suggest the use of emulsions to separate $CO_2$ from blood.

SUMMARY OF THE INVENTION

A novel process for oxygenating blood has now been unexpectedly discovered, which comprises contacting the blood with an emulsion, said emulsion comprising an oxygen-containing fluorinated organic exterior phase, surrounding droplets of an aqueous interior phase, whereby the oxygen permeates from the fluorinated organic exterior phase into the blood and the carbon dioxide in the blood permeates through the fluorinated organic exterior phase into the aqueous interior phase. The driving force for these permeations results from the differing pressures of both oxygen and carbon dioxide in the various phases. Thus, the high partial pressure of carbon dioxide in the blood will drive carbon dioxide through the fluorinated organic exterior phase into aqueous interior phase, wherein, preferably, a carbon dioxide absorbent or the substance capable of reacting with carbon dioxide and converting it into a nonpermeable form is contained. For example, sodium carbonate can be contained in the interior phase of the emulsion which converts $CO_2$ to sodium bicarbonate which will not permeate through fluorinated organic external phase into the blood.

To oxygenate blood according to the process of the instant invention the following procedure is followed: An emulsion of an aqueous solution containing a carbon dioxide absorbent or reactant, in a fluorinated organic exterior phase, is prepared by mixing said aqueous solution with said fluorinated organic compound under conditions of sheer. Preferably, a surfactant which is soluble in the fluorinated organic phase is utilized to make the emulsion stable for further use. The surfactant, of course, must be compatible with blood. Preferably, fluorinated surfactants are utilized, most preferably the surfactants are perfluorinated.

The surfactant as stated above should not damage blood. Perfluorinated surfactants are especially preferred for this reason. The surfactants may be extended in a fluorinated organic solvent which will form the external phase or the surfactant, itself, can be the external phase. Usually, however, a fluorinated organic solvent will be utilized as the major portion of the external phase.

The emulsion is made by conventional techniques, including use of colloidal mills, simple mixers, homogenizers, and ultrasonic devices as described in detail in Chapter 7 of "*Emulsions: Theory and Practice*" by Paul Becher, published by Reinhold Publishing Corporation, - 1965. After the stable emulsion is formed, it is contacted with a source of gaseous oxygen. Preferably, oxygen is added to the emulsion until saturation is achieved. Oxygen is known to the prior art to be extremely soluble in various fluorinated organic solvents and these solvents are preferred in the instant process. The fluorinated organic solvents which may be utilized include: fluorinated ethers, amines, carboxyl esters, carboxylic acids, aldehydes, alcohols, ketones and etc. Fluorinated derivatives of saturated and unsaturated hydrocarbons, including alkenes, alkynes, and aromatics, as well as the chloro, bromo, and iodo derivatives thereof may be utilized in the practice of the instant invention. Preferably the above compounds are perfluorinated, i.e. all the hydrogen radicals are replaced by fluorine radicals.

The above described compounds must be liquid at the temperatures at which the instant process will be operated i.e. from about 4° to 35/20 C., preferably from about 10° to 20°C., thus these compounds will contain from 1 to 40 carbon atoms, preferably from 5 to 20 carbon atoms.

Because of their inertness toward blood, the most preferred fluorinated organic compounds are the perfluorinated hydrocarbon derivatives, having from 5 to 20 carbon atoms.

The emulsion is contacted with blood either in a concurrent or counter concurrent manner. Agitation is applied to the blood emulsion system so that the emulsion breaks up into droplets, said droplets being contacted with blood at the fluorinated organic blood interface. In this manner, carbon dioxide present in the blood wil permeate through the fluorinated organic exterior phase and into the aqueous droplets wherein it will be absorbed or converted to a nonpermeable species. The oxygen dissolved in the fluorinated organic external phase will continuously permeate into the blood thus resulting in a process for simultaneously oxygenating blood while removing carbon dioxide. When the blood has been fully oxygenated, agitation may be stopped at which time the blood and the emulsion will separate because of the difference in densities of said blood and said emulsion. Usually the emulsion will settle to the bottom of the contacting vessel where it may be collected and regenerated by breaking the emulsion and re-emulsifying a new aqueous adsorbent or reactant. The blood will then be returned to the body.

It is important that the emulsion be stable during the contacting with blood since breaking will allow the blood to mix with the aqueous droplets, thereby mixing the $CO_2$ absorbent or reactant with the blood.

Any surface active agent which is capable of forming a stable emulsion with the fluorinated organic solvent and the aqueous absorbent or reactant solution, may be utilized to form the emulsion of the instant invention. Preferred surfactants are fluorinated surfactants, more preferably perfluorinated surfactants, and include fluorinated esters, fluorinated amines, fluorocarboxylic acids, fluorosulfonic acids, etc. In general, the perfluorinated surfactants may be chosen from the same class of compounds as the above described solvents, however, they will be the surface active members of the above-defined group.

The surfactant should be soluble in the fluorinated organic exterior phase and have insignificant solubility in water since solubility in any signficant amount, in either the blood or $CO_2$ absorbent interior phase, is undesirable. Preferred fluorinated surfactants are the fluorinated ethers, esters and carboxylic acids having a carbon number of from 5 to 25, more preferably the surfactants are perfluorinated derivatives having a carbon number of from 5 to 15. The solvent and surfactant mixture is of course chosen to be permeable to carbon dioxide while solubilizing as much oxygen as possible.

The preferred method of use for the process of the instant invention comprises separating venous blood from a human body by shunting said venous blood prior to its return to the heart. Venous blood will be characterized as having a greater amount of carbon dioxide than arterial blood and a corresponding lower concentration of oxygen. The blood will be shunted from the body into a contacting zone wherein said aforedescribed emulsion will be contacted with said blood. The carbon dioxide wil be removed simultaneously with the oxygenation of the blood. After sufficient oxygen is returned to the blood and sufficient carbon dioxide is removed, the blood will be returned to the body for reuse. Normally venous blood contains about 53 volume percent carbon dioxide and about 15 volume percent of oxygen. Desirably about 20 volume percent of oxygen should be present in the arterial blood and less than 50 volume percent of carbon dioxide. Thus, the process of the instant invention pertains to a process whereby additional oxygen is forced into the blood while excess carbon dioxide is removed.

Preferably sodium carbonate is present in the interior phase of said emulsion to react with the $CO_2$. Use of $Na_2CO_3$ is preferred for safety reasons, since in the event that said emulsion partially breaks small amounts of sodium carbonate, mixing with the blood, would not cause a drastic effect.

The instant invention provides for certain advantages. For example, blood denatuation is avoided because the proteins in the blood are not in direct contact with bulk oxygen. $CO_2$ removal from the blood is rapid becasue of the presence within the droplet, i.e. the interior phase of the emulsion, of a material capable of reacting with or absorbing the $Co_2$. This allows for the maintenance of a concentration difference between the blood and the interior phase of the emulsion. If said material was absent, $CO_2$ would permeate into the interior phase of the emulsion only to the point where the concentration in the interior phase and the blood was equal. At this point further permeation would cease. Utilization of absorbents or reactants to remove $CO_2$ in the interior phase of the emulsion provides unlimited capacity. A further advantage of the instant invention over the prior art is that since the emulsion is contacted with the blood under conditions of agitation, whereby the emulsion is broken up into droplets, increased surface area is available for exchange of oxygen and $CO_2$. The process of the instant invention, thus shows increased exchange rates when compared to the prior art system where blood and the fluorocarbon is contacted by countercurrent flow, at conditions of minimum agitation. The surfactants present further enhance contact by breaking the emulsion into smaller droplets than would be possible in a straight fluorinated organic solventblood exchange system and thus further increasing the contact area.

In the usual process of the instant invention, the blood is a continuous phase and the emulsion is dispersed uniformly throughout by agitation. Said agitation may be provided by countercurrent flow as well as mechanical forces. The emulsion system may be continuously reused until the oxygen is depleted and/or the carbon dioxide adsorbent or reactant is used up. When this occurs, the emulsion is sent to a separate treating zone wherein the emulsion is broken to separate the spent aqueous interior phase, while the fluorinated organic exterior phase, including surfactant, is recycled for use in preparing a fresh emulsion. It is also possible, when sodium carbonate is utilized to react with the carbon dioxide, to recycle emulsion without breaking. In recycling this specific emulsion, heat may be used to decompose the sodium bicarbonate to $CO_2$ and $Na_2CO_3$ without breaking the emulsion. The carbon dioxide is removed and the sodium carbonate containing emulsion is returned for reuse.

Other materials which may be utilized as the absorbent or reactant for $CO_2$ include the following: inorganic or organic basic materials such as calcium hydroxide, sodium hydroxide, magnesium hydroxide, potassium hydroxide, amines, such as alkyl and aryl, mono- and polyamines, preferably having from 1 to 20 carbons, and derivatives thereof, alkali metal and alkaline earth carbonate salts such as potassium carbonate, etc. Of course it is possible to use water alone as the aqueous phase since $CO_2$ is soluble in water. As mentioned above, however, it is preferable to have a reactant and an absorbent to maintain a concentration difference of $CO_2$ in the blood and in the interior phase.

The contacting of the blood and the emulsion takes place at a temperature range from about 4 to 35°C., preferably from 10 to 20°C. and a pressure of 1 atmosphere. Contact times are not critical and may vary to maintain desirable oxygen and carbon dioxide concentrations in the blood flowing out of the contacting zone. In a typical process, venous blood, which contains 15 volume percent oxygen and 55 volume percent of $CO_2$, is contacted with aforedescribed emulsion. Upon leaving the contacting zone, said blood contains 20 volume percent oxygen and 40 volume percent $CO_2$. The above process is run in a continuous manner. The blood, after contacting with the emulsion, is returned to the patient's body through an artery in said patient's arm. After contacting the interior aqueous phase may be still capable of absorbing $CO_2$ and/or reacting with $CO_2$ while the oxygen in the exterior phase is spent. In this case, the emulsion may be returned and reoxygenated by bubbling oxygen through the emulsion at any practical rate without the need for breaking the emulsion and/or regenerating said aqueous $CO_2$ absorbent or reactant. When the interior aqueous phase is also spent, the emulsion may be broken and the interior phase replaced. Alternately, the spent aqueous phase may be regenerated separately and used for forming a fresh emulsion.

The following is a specific embodiment of the instant invention.

In this specific example of the instant invention, blood in the amount of 610 grams, was oxygenated.

The emulsion utilized was 200 grams of an aqueous solution of $Na_2CO_3$ 5 %/weight/ and 284 grams of a mixture of fluorinated organic compounds. The fluorinated organic compounds which formed the exterior phase of the emulsion contained 5% of a fluorinated $C_{14}$ ether surfactant manufactured by duPont under the Trade name Freon E-4

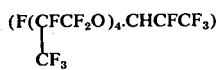

and 95% by weight of perfluorotributylamine. The system was emulsified by slowly pouring the sodium carbonate solution into the surfactant solution while a stirring speed of 600 RPM was maintained so that the two solutions were rapidly emulsified as soon as they come in contact. The emulsification was carried out at 25°C. Included within the system, to help stabilize the emulsion were 0.2 gms. of Fluorad FC-170, a fluorochemical surfactant, utilizing a fluorinated hydrocarbon tail, manufactured by 3M. The use of Fluorad FC-170 is optional.

The emulsion was contacted with the blood at 25°C. in a batch process.

The oxygen content of the blood, initially, in mm of mercury was 10.5 and the $CO_2$ content was very high as indicated by the low blood pH of 6. The oxygen was analyzed by a physiological gas analyzer with oxygen electrode manufactured by the Veri-Flor Corporation. When the emulsion passed through the blood phase once, the oxygen concentration in blood was drastically increased to 275. Some of the oxygen might have escaped during the time of preparing the second pass of the emulsion, because the oxygen concentration was dropped slightly to 220 at the beginning of the second pass of the emulsion through the contactor. However, the oxygen concentration immediately began to reverse again when the re-oxygenated emulsion was sent to the blood oxygenator for a second pass. At the end of the second pass, the oxygen concentration increased up to 300 mm Hg.

In the experiment, the emulsion was reoxygenated after it was passed through the blood oxygenator once. It was not necessary to regenerate the aqueous $Na_2CO_3$ solution since excess $Na_2CO_3$ was used.

The carbon dioxide concentration in the blood decreased as indicated by the change of pH value which increased from 6 to a value between 7 and 8 (around 7.5 ) as shown in the following Table. This pH indicates that the $CO_2$ concentration in the oxygenated blood was drastically reduced.

TABLE

| | Analyzing Time (Min.) | Oxygen Concentration in Blood (mm Hg) |
|---|---|---|
| I. First Pass of the Emulsion through the blood oxygenator | 0 | 10.5 |
| | 1 | 10.5 |
| | 4 | 12.5 |
| | 5 | 12.5 |
| | 6 | 80 |
| | 7 | 120 |
| | 8 | 200 |
| | 9 | 270 |
| | 18 | 290 |
| | 27 | 275 |
| II. Second Pass of the Emulsion through the blood oxygenator | 0 | 220 |
| | 2 | 340 |
| | 5 | 340 |
| | 7 | 360 |
| | 8 | 380 |
| | 12 | 300 |

At the end of the first pass of the emulsion, no further change of the pH value was noticed at the end of the second pass of the emulsion, indicating the removal of $CO_2$ must be so rapid that the removal was essentially completed during the first pass of the emulsion.

What is claimed is:

1. A process for oxygenating human blood and simultaneously removing $CO_2$ which comprises separating venous blood from a human body by shunting said venous blood prior to its return to the heart, contacting said shunted blood in a contacting zone, with an emulsion, the exterior phase which is liquid at a temperature of from 4° to 35°C and which comprises a $C_1$ to $C_{40}$ fluorinated organic compound, said exterior phase further comprising dissolved oxygen, surrounding aqueous droplets, whereby said oxygen permeates into said blood and the $CO_2$ in said blood permeates into said aqueous droplets, and returning said blood having increased oxygen content and decreased $CO_2$ content to said human body.

2. The process of claim 1 wherein said contacting takes place at a temperature of from 4° to 35°C.

3. The process of claim 1 wherein said aqueous droplets contain a $CO_2$ absorbent.

4. The process of claim 1 wherein said aqueous droplets further comprise a reactant capable of reacting with $CO_2$.

5. The process of claim 4 wherein said reactant comprises sodium carbonate.

6. The process of claim 4 wherein said exterior phase comprises a $C_1$ to $C_{40}$ fluorinated organic solvent and a $C_5$ to $C_{25}$ fluorinated surfactant.

7. The process of claim 6 wherein said surfactant and said solvent are perfluorinated.

8. The process of claim 6 wherein said surfactant contains from 5 to 20 carbons and is selected from the group consisting of fluorinated ethers, esters and carboxylic acids.

* * * * *